United States Patent
Douglas et al.

(10) Patent No.: US 11,244,758 B2
(45) Date of Patent: Feb. 8, 2022

(54) SELF-VALIDATING MODULE FOR SOFTWARE CONTROL OF MEDICAL DEVICES

(71) Applicant: White Bear Medical LLC, White Bear Lake, MN (US)

(72) Inventors: Ryan Douglas, Stillwater, MN (US); Steven Gigl, Crystal, MN (US); Jonathan Lawson, Cottage Grove, MN (US); James Kinney, Mahtomedi, MN (US); David Bontrager, Minneapolis, MN (US)

(73) Assignee: White Bear Medical, LLC, White Bear Lake, MN (US)

( * ) Notice: Subject to any disclaimer, the term of this patent is extended or adjusted under 35 U.S.C. 154(b) by 1099 days.

(21) Appl. No.: 15/486,166

(22) Filed: Apr. 12, 2017

(65) Prior Publication Data

US 2017/0293731 A1    Oct. 12, 2017

Related U.S. Application Data

(60) Provisional application No. 62/321,616, filed on Apr. 12, 2016.

(51) Int. Cl.
*G06Q 50/00* (2012.01)
*G16H 40/63* (2018.01)
*G16H 50/20* (2018.01)

(52) U.S. Cl.
CPC ............ *G16H 40/63* (2018.01); *G16H 50/20* (2018.01)

(58) Field of Classification Search
CPC ....... A61M 5/14244; A61N 1/00; A61B 6/548
USPC ......... 705/2, 3; 607/60; 340/568.1; 600/300; 702/114; 717/171
See application file for complete search history.

(56) References Cited

U.S. PATENT DOCUMENTS

| | | | |
|---|---|---|---|
| 6,950,708 B2 * | 9/2005 | Bowman, IV | A61N 1/37211 607/60 |
| 9,486,571 B2 * | 11/2016 | Rosinko | A61M 5/14244 |

(Continued)

OTHER PUBLICATIONS

Google patents search, Nov. 1, 2019 (Year: 2019).*

(Continued)

*Primary Examiner* — Dilek B Cobanoglu
(74) *Attorney, Agent, or Firm* — Craige Thompson; Thompson Patent Law; Timothy D. Snowden

(57) ABSTRACT

Apparatus and associated methods relate to a Self-Validating System (SVS) which includes an Electronic Self-Validating Module (ESVM) that may be employed within a medical device, operable to receive and to transmit wireless transmissions to and from a personal electronic mobile device, the mobile device executing a Self-Validating Medical Device Remote Control (SVMDRC) application, also known as the mobile app, operable to control the ESVM, the mobile device and the ESVM further executing a pre-determined sequence of instructions at a pre-determined frequency, operable to perform a set of safety (validation) checks on the mobile device, and the ESVM. In an illustrative example, changes (updates) to the mobile device's operating system, the app, or the hardware on the mobile device may be detected by the mobile device, and may advantageously re-validate the mobile device automatically.

20 Claims, 8 Drawing Sheets

(56) References Cited

U.S. PATENT DOCUMENTS

| | | | | |
|---|---|---|---|---|
| 2003/0025602 A1* | 2/2003 | Medema | ................ | G16H 40/20 340/568.1 |
| 2008/0312512 A1* | 12/2008 | Brukalo | ............ | A61M 5/14244 600/300 |
| 2012/0197580 A1* | 8/2012 | Vij | ........................ | A62B 27/00 702/114 |
| 2013/0086573 A1* | 4/2013 | Moritzen | ................. | G06F 8/65 717/171 |
| 2017/0150939 A1* | 6/2017 | Shah | ...................... | G16H 40/67 |

OTHER PUBLICATIONS

Google patents search, Dec. 22, 2020 (Year: 2020).*
Google patents search, Jun. 3, 2021 (Year: 2021).*
Ip.com search, Sep. 25, 2021 (Year: 2021).*

* cited by examiner

SELF-VALIDATING MODULE FOR SOFTWARE CONTROL OF MEDICAL DEVICES

CROSS-REFERENCE TO RELATED APPLICATIONS

This application claims the benefit of U.S. Provisional Application Ser. No. 62/321,616 titled "Self-Validating Module for Software Control of Medical Devices," filed by Ryan Douglas, et al. on Apr. 12, 2016.

This application incorporates the entire contents of the foregoing application(s) herein by reference.

TECHNICAL FIELD

Various embodiments relate generally to medical device compliance.

BACKGROUND

Doctors and other clinicians have benefited from the use of medical devices to aid in medical procedures and to provide therapy to their patients. Various medical devices may be employed to provide diagnostic measurement. For example, blood oxygen monitors may be used to monitor a patient's blood oxygen levels during a surgical procedure, so that anesthesiologists may ensure a patient is receiving proper levels of anesthesia and oxygen. Medical devices may also be employed to provide various kinds of therapy. For example, kidney dialysis devices may provide a type of blood filtration, providing patients with some of the functionality of a once healthy kidney. Many modern medical devices employ state of the art electronics to provide their desired functionality. Often, modern electronic medical devices employ software to provide the device functionality, or to provide sub-functions. Medical devices have been designed to be employed almost anywhere. They can be found, for instance, in hospitals, clinics, and homes. In the case of mobile medical devices such as pacemakers and insulin pumps, medical devices may be found in vehicles, and may be personally attached and carried on a patient as they go about their daily activities.

To ensure safety and efficacy, regulating bodies (for example the Food and Drug Administration (FDA)) involve themselves in the development and manufacture of medical devices, specifying regulations in published standards. Developers and manufacturers are required by law to comply with those standards. During the development of a medical product, in order to provide proof of compliance to the standards, developers may author and employ various test rigors defined as "design validation." During manufacture as well, various manufacturing processes may be under the scrutiny of the regulatory agencies, and may be required to comply with published standards. As part of regulatory compliance, manufacturers may author and employ various test rigors defined as "production validation."

Once the design and manufacture of a medical device has been validated, the device may be produced and delivered to end customers as a validated product. The products as shipped from the manufacturer remain validated unless something in the manufacture or the design is altered, at which point the test rigors may be required in order to re-validate the product. For example, if a component within the medical design goes obsolete, and a new similar component is employed as a drop-in replacement, at least a subset of the original design validation testing may be required to prove the safety and efficacy of the product with the new component. In some examples, when the programming is changed within any programmable device within the medical device system, re-validation testing may be required.

SUMMARY

Apparatus and associated methods relate to a Self-Validating System (SVS) which includes an Electronic Self-Validating Module (ESVM) that may be employed within a medical device, operable to receive and to transmit wireless transmissions to and from a personal electronic mobile device, the mobile device executing a Self-Validating Medical Device Remote Control (SVMDRC) application (also known as the mobile app) operable to control the ESVM, the mobile device and the ESVM further executing a pre-determined sequence of instructions at a pre-determined frequency, operable to perform a set of safety (validation) checks on the mobile device, and the ESVM. In an illustrative example, changes (updates) to the mobile device's operating system, the app, or the hardware on the mobile device may be detected by the mobile device, and may advantageously re-validate the mobile device automatically.

Various embodiments may achieve one or more advantages. For example, some embodiments, including a medical device operated by a user on a mobile device, may, on an ongoing basis, validate that the mobile device running an SVMDRC app is in a validated state.

In some embodiments, a mobile device running an SVMDRC app may command the medical device to go to a safe state upon detection of a change in qualified state (e.g., updated app version or updated Operating System (OS)). In an illustrative example, users may download the latest version of the "medical device remote control" app customized to medical device they wish to control, onto any compatible mobile device. Once downloaded and installed, the user may run the app to gain remote control functions of their medical device. As the app is running, built-in functionality within the app may provide periodic self-validating functions. For example, the app may query the OS for a Unique Device Identifier (UDID) and the OS version number and may compare those with a list of acceptable UDID & OS pairs. If the self-validating function within the app determines the identifier and/or the version are not acceptable, the app may command the medical device to go into a default safe state. In some examples, when the self-validating function within the app determines the identifier and/or the version are not acceptable, the app may stop communicating, and allow the medical device to determine it needs to go to a safe state.

In various exemplary embodiments, the SVS may enable developers and manufacturers of medical devices to reduce the burden of on-going validation testing within the development facility.

In some embodiments, multiple mobile device types may be inter-operable allowing the mobile device app to work with many different mobile devices designed and built with many different manufactures. In an illustrative example, an end-user of a medical device may have been controlling their medical device with a Brand A mobile device. Later, the end user changes to a new mobile device, Brand B. The end user may continue to use the SVMDRC app on the Brand B phone, as the application may validate the compatibility of the mobile device brand and model using the mobile device's UDID, as well as validate the compatibility and functionality of the mobile device's hardware (e.g., user interfaces, memory, and communication transceivers).

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, an exemplary system implementation is briefly introduced with reference to FIG. 1. The exemplary system includes a remote handheld device, for example, a mobile phone, and a medical device, in communication with one another. Next, a more detailed description is provided for the medical device in FIG. 2 and the mobile device in FIG. 3. Next, more detail is presented around the main software functionality of the medical device in FIG. 4 and of the mobile device in FIG. 5. FIG. 6 provides detail around the self-validation functionality for both the medical device and the mobile device. Some description of an exemplary risk assessment is presented in FIG. 7, providing some detail around the decisions behind certain mitigation levels. Finally, in FIG. 8 an illustrative example of the deployment of a mobile app to the mobile devices (including the cloud-based servers) is depicted.

Figure 1:
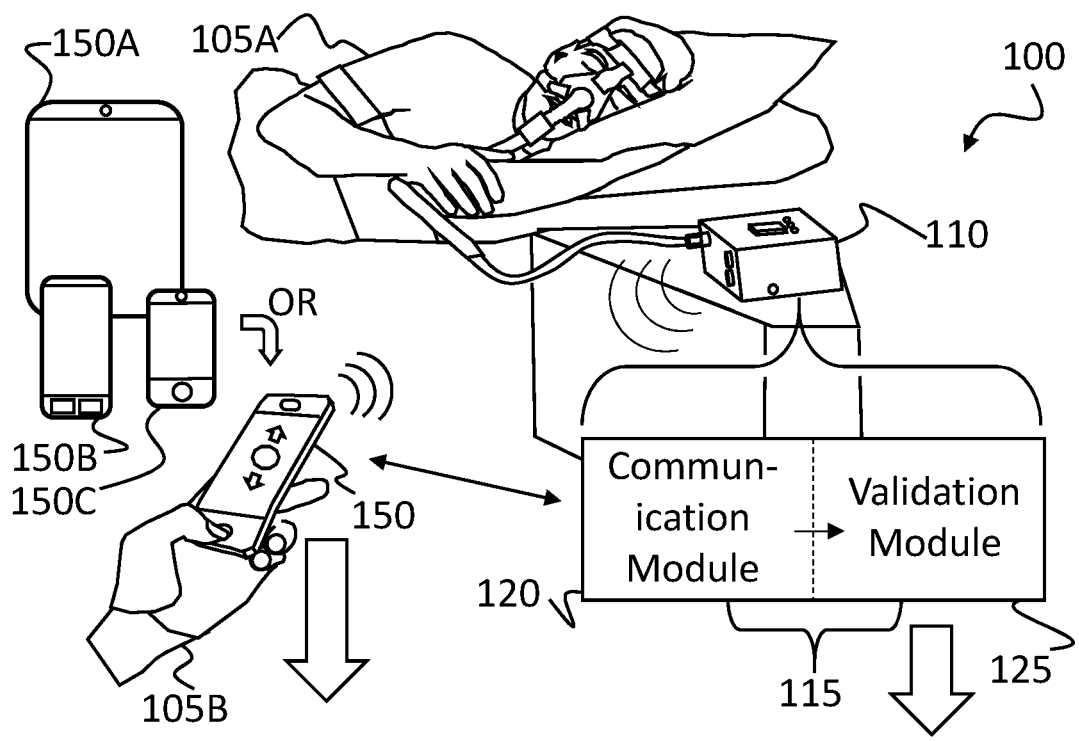
FIG. 1 depicts a use case and block diagram of an exemplary Self-Validating System (SVS).
Figure 1:
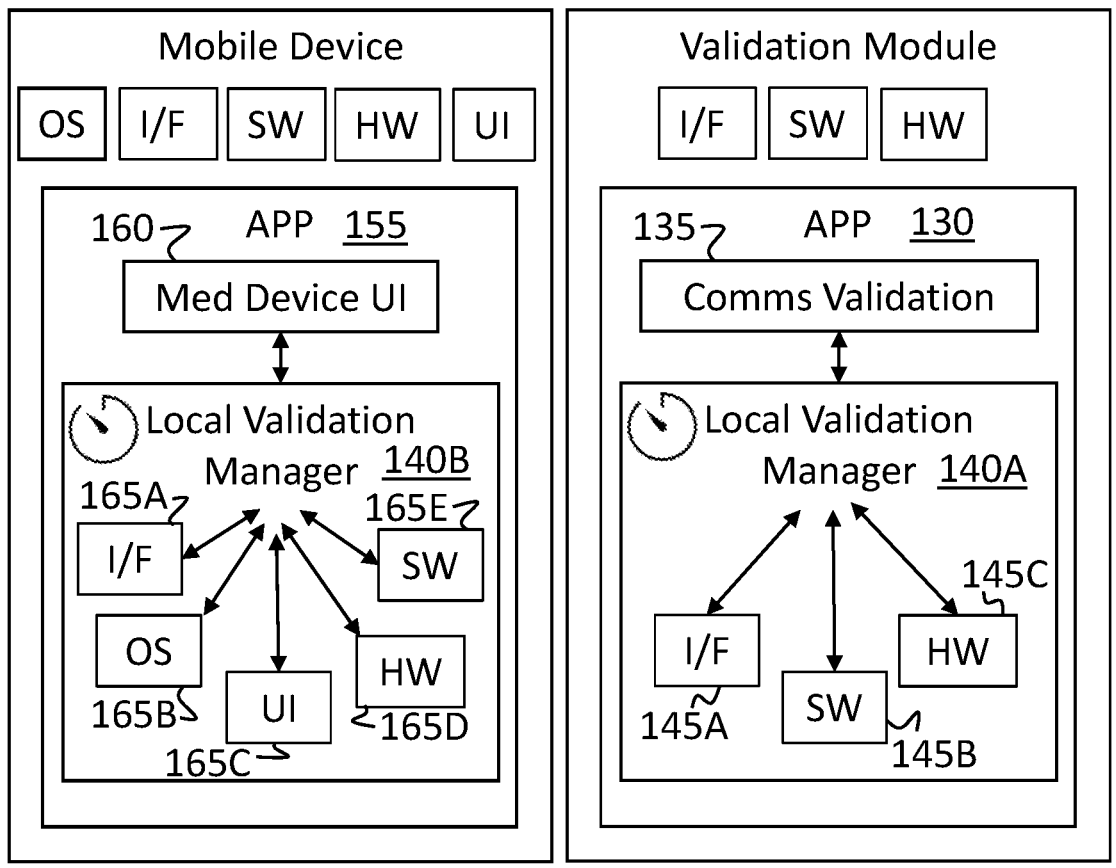

FIG. 1 depicts a block diagram and use case of an exemplary Self-Validating System (SVS). An exemplary use case 100 includes a patient 105A. The patient 105A is wearing a medical device 110. The patient 105A is receiving respiratory therapy from the medical device 110, which is controlled by a mobile device 150. The medical device 110 is also controllable by mobile devices of various manufacturers and models 150A, 150B and 150C. The medical device 110 includes an Electronic Self-Validating Module (ESVM) 115. The mobile device 150 executes a Self-Validating Medical Device Remote Control (SVMDRC) application (also known as the mobile app) operable to controlling the ESVM 115. The mobile device 150 and the ESVM 115 further execute a pre-determined sequence of instructions at a pre-determined frequency, which perform a set of safety (validation) checks on the mobile device 150 and the ESVM 115. The ESVM 115 includes a communication module 120 and a validation module 125. The validation module 125 includes an app 130. The app 130 runs a communication validation routine 135. The communication validation routine 135 is governed by a local validation manager 140A. The local validation manager 140A schedules and manages a set of validation tasks. In the depicted example, the local validation manager 140A schedules and manages the validation of at least three mechanisms containing components whose functionality may affect the safety of the SVS: an interface 145A, a software module 145B, and a hardware module 145C. In some examples, changes (updates) to the mobile device's operating system, the app, or the hardware on the mobile device may be detected by the mobile device, and may advantageously re-validate the mobile device automatically.

The medical device 110 is operably controlled by the mobile device 150. The mobile device 150 is operated by a user 105B. The mobile device 150 includes an app 155. The app 155 runs a medical device user interface 160. The medical device user interface 160 is governed by a local validation manager 140B. The local validation manager 140B schedules and manages a set of validation tasks. In the depicted example, the local validation manager 140B schedules and manages the validation of at least five mechanisms containing components whose functionality may affect the safety of the SVS: an interface 165A, an operating system 165B, a user interface 165C, a hardware module 165D, and a software module 165E.

Figure 2:
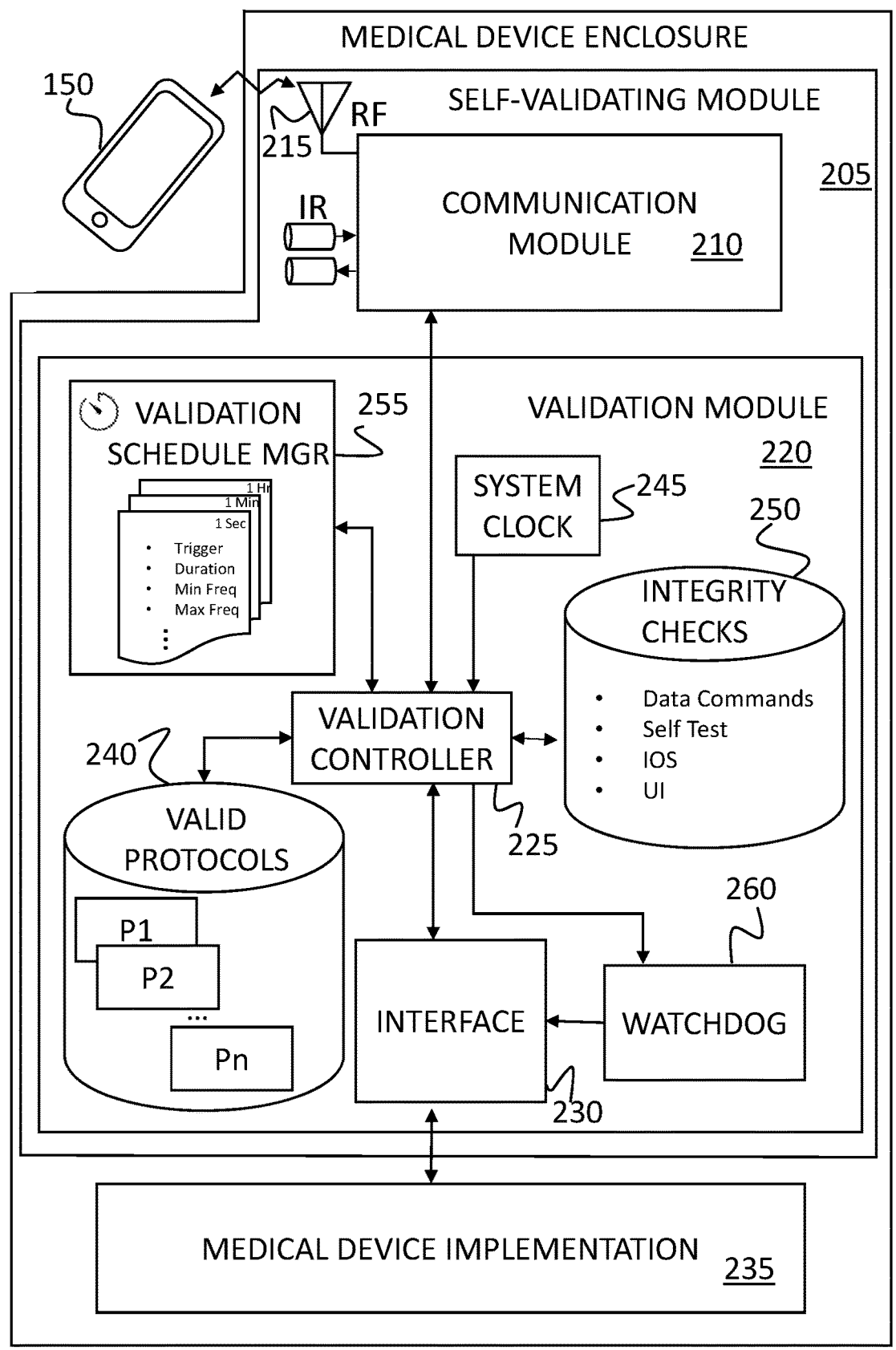
FIG. 2 depicts a block diagram view of an exemplary medical device.

FIG. 2 depicts a block diagram view of an exemplary medical device. A medical device 200 includes an ESVM 205. The ESVM 205 includes a communication module 210 and a validation module 220. The communication module 210 is electrically connected to an antenna 215. In operation, the mobile device 150 communicates with the communication module 210 via the antenna 215. The communication module 210 is electrically connected to the validation module 220. Received commands from the communication module 210 are sent to a validation controller 225 where they are examined for their validity. Valid commands make their way to an interface 230. The interface 230 is electrically connected to a medical device implementation 235.

In an illustrative example, the ESVM 205 may be employed within the medical device 200. The ESVM 205 may be operable to receive and to transmit wireless transmissions to and from the mobile device 150. The mobile device 150 may execute a SVMDRC application operable to controlling the ESVM 205 in a safe and validated manner.

Control commands from the mobile device 150 make their way wirelessly to the medical device 200. At the medical device 200, the commands are sent to the validation controller 225 operatively allowing only valid commands (as qualified by comparison to a valid protocols database 240) to pass through to the interface 230 and eventually to the medical device implementation 235.

The validation controller 225 (driven by a system clock 245) provides self-validation features in addition to filtering commands from the mobile device 150. The validation controller 225 is operably coupled to an integrity check database 250. The integrity check database 250 provides the validation controller a list of tasks to perform to validate its own hardware and software. The validation controller 225 executes a predetermined sequence of instructions to perform scheduled validation tasks by employment of a validation schedule manager 255. The validation controller 225 employs a hardware watchdog 260. The hardware watchdog 260 receives an electrical "heartbeat," which is tied to a main execution loop. Should the validation controller 225 cease to execute all of its expected steps, the heartbeat would fail to beat, and the hardware watchdog 260 would block the interface from the validation controller 225 to the medical device implementation 235. With such a configuration, commands may be passed through the validation module 220 only if the validation controller 225 is operating properly.

Figure 3:
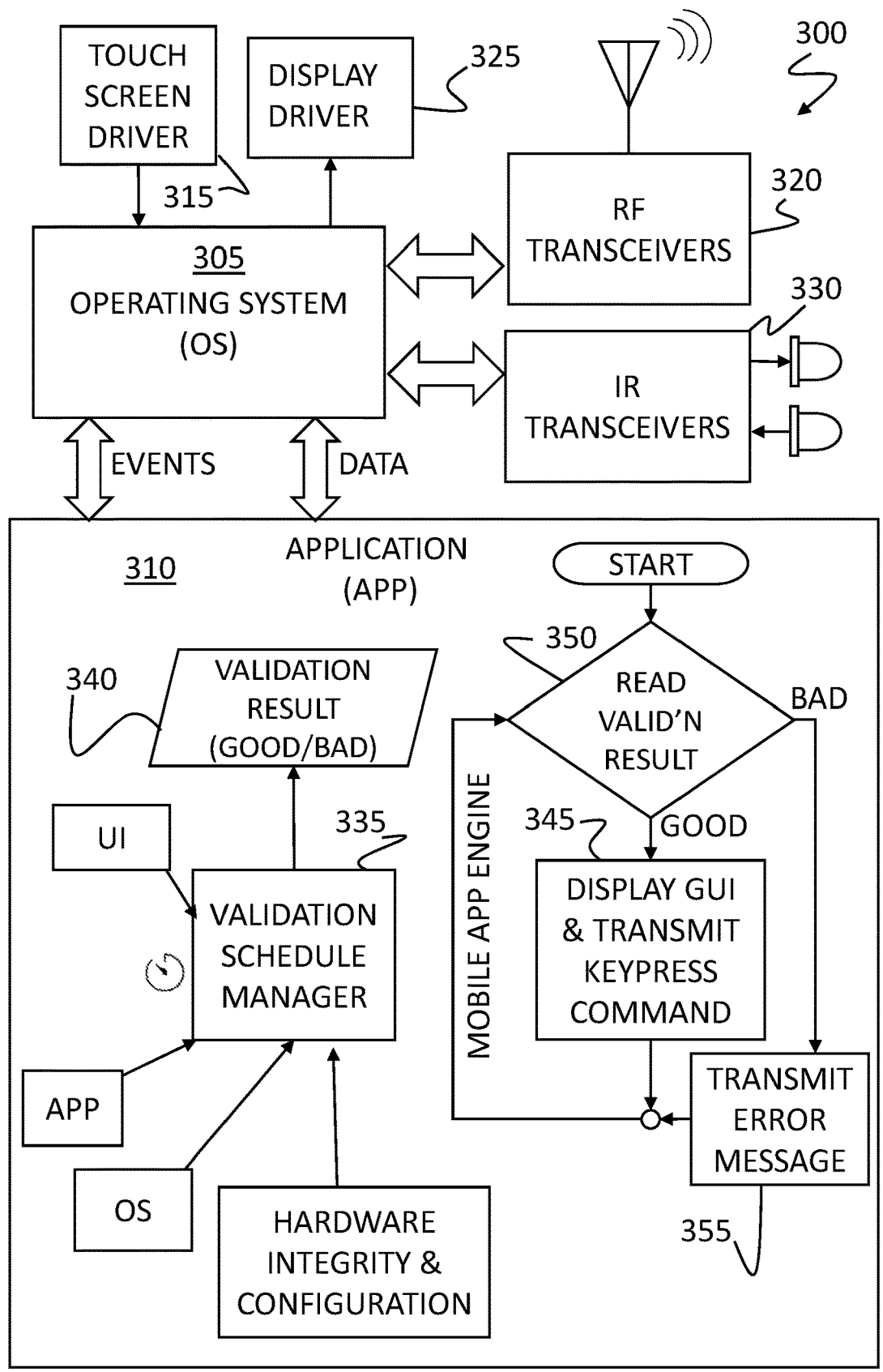
FIG. 3 depicts a data flow diagram of an exemplary mobile device.

FIG. 3 depicts a data flow diagram of an exemplary mobile device. At the center of a mobile device dataflow diagram 300 is an operating system 305. The operating system 305 also makes events and data available to an application (app) 310. The events include "finger press" and "swipe" events from the touch screen driver 315. The events also include serial data reception events from an RF transceiver 320. Data from the RF transceivers 320 is also shared from the operating system 305 to the app 310.

In this example, the operating system 305 in the mobile device dataflow diagram 300 manages a display driver 325. The mobile device dataflow diagram 300 also includes an infrared (IR) transceiver 330. The IR transceivers 330 may be used for communication to a medical device. In the depicted example, the app 310 is split into two main tasks. One task schedules validation activities 335 and manages a validation result 340. A second task performs the main GUI management and keypress transmissions 345. In the second task, the validation result from the first task is read 350. If the validation result is bad (e.g., validation checks have failed) then the app 310 transmits an error message 355 to the medical device. A more detailed description is contained in FIGS. 4 and 5, as described below.

Figure 4:
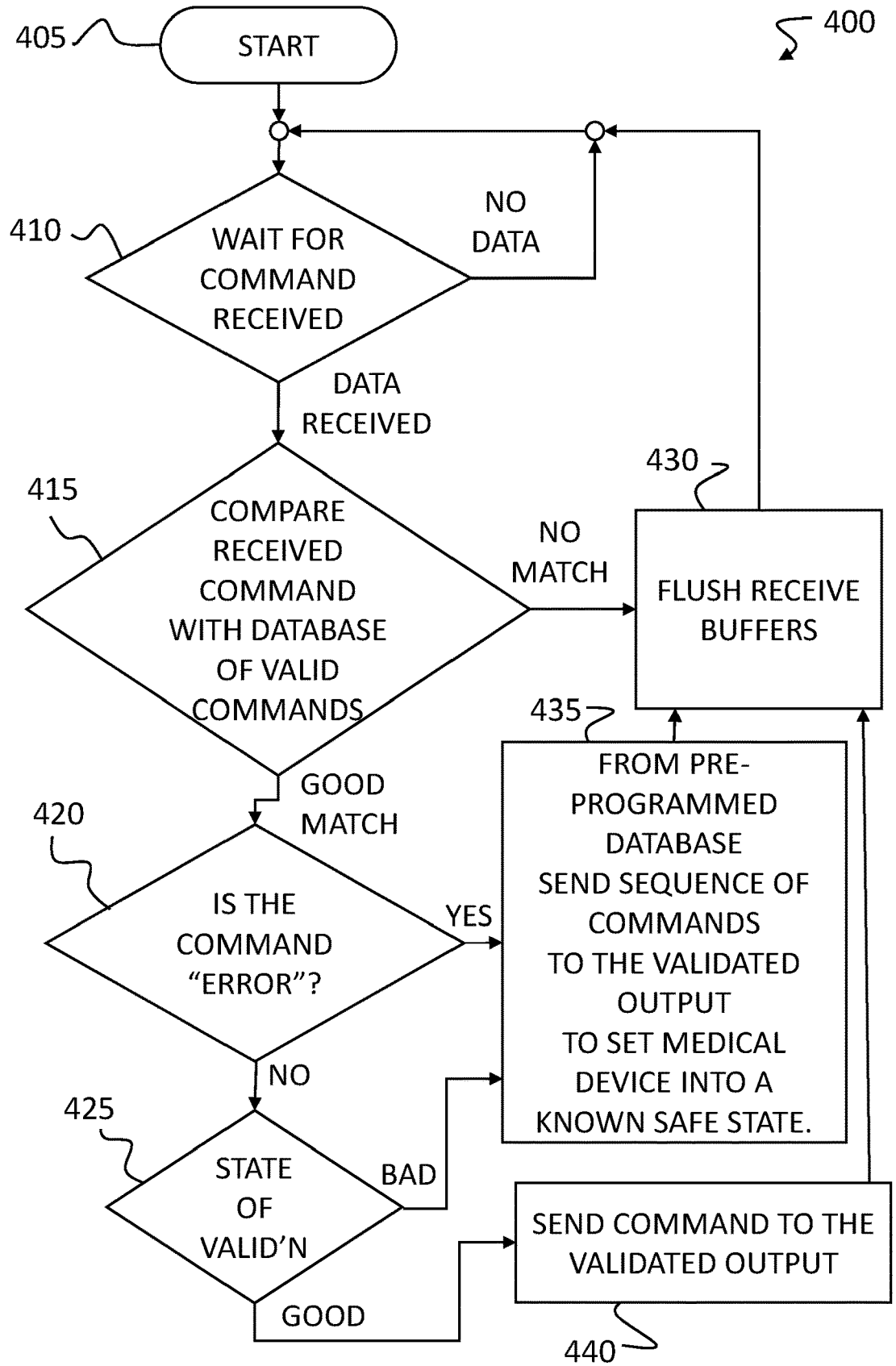
FIG. 4 depicts a flowchart of a command validation routine of an exemplary Electronic Self-Validating Module (ESVM).

FIG. 4 depicts a flowchart of a command validation routine of an exemplary Electronic Self-Validating Module (ESVM). An ESVM may be employed within a medical device, providing validation activities with in an SVS. The ESVM communicates to a remote device (e.g., mobile phone, electronic tablet) allowing the remote device to control the host medical device which includes the ESVM within its electronic design. Within the ESVM is an electronic processor which validates commands from the remote device, sending only validated commands from the remote device to the medical device, which may advantageously provide validated safety to a patient. In addition to validating commands from the remote device, the electronic processor may validate its own hardware and software, allowing a validated module to control the medical device.

A command validation routine 400 includes an entry point 405. The entry point 405 directs control to a wait loop 410. The wait loop 410 waits for commands from a remote device. If the remote device sends a wireless command to the ESVM, the software detects it (DATA RECEIVED) at the wait loop 410 and control continues to a validity check decision 415. If at the wait loop 410, no data is received (NO DATA) from the remote device, control continues back to the wait loop 410.

Once data is received, control is directed to the validity check decision 415. The validity check decision 415 compares the received command from the remote device with a database of valid commands. If the command received does not match a valid command from the database (NO MATCH), control is directed to a buffer flush subroutine 430, where the receive buffer is cleared. Control is then directed back to the wait loop 410, where the ESVM waits for the next command from the remote device. If the command received does match a valid command from the database (GOOD MATCH), control is then directed to a check for error decision 420.

At the check for error decision 420, the command validation routine 400 checks for a specific command. If the remote device signals a validated error command, the ESVM directs control to a safe state subroutine 435 which sends a sequence of commands to the validated output from a pre-programmed database, to set the medical device into a known safe state. Buffers are then flushed in the buffer flush subroutine 430, and control is directed back to the wait loop 410. If the remote device is not signaling an error command, the command validation routine 400 continues by checking a state of validation 425. The state of validation may be managed by a separate software engine which checks various hardware and software functionality and appropriately sets a validation state variable, which is checked here at the state of validation 425.

If the state of validation 425 is bad, control is directed to the safe state subroutine 435. If the state of validation 425 is good, control is directed to sending out the command to a validated output 440 of the ESVM. Buffers are then flushed in the buffer flush subroutine 430, and control is directed back to the wait loop 410.

Figure 5:
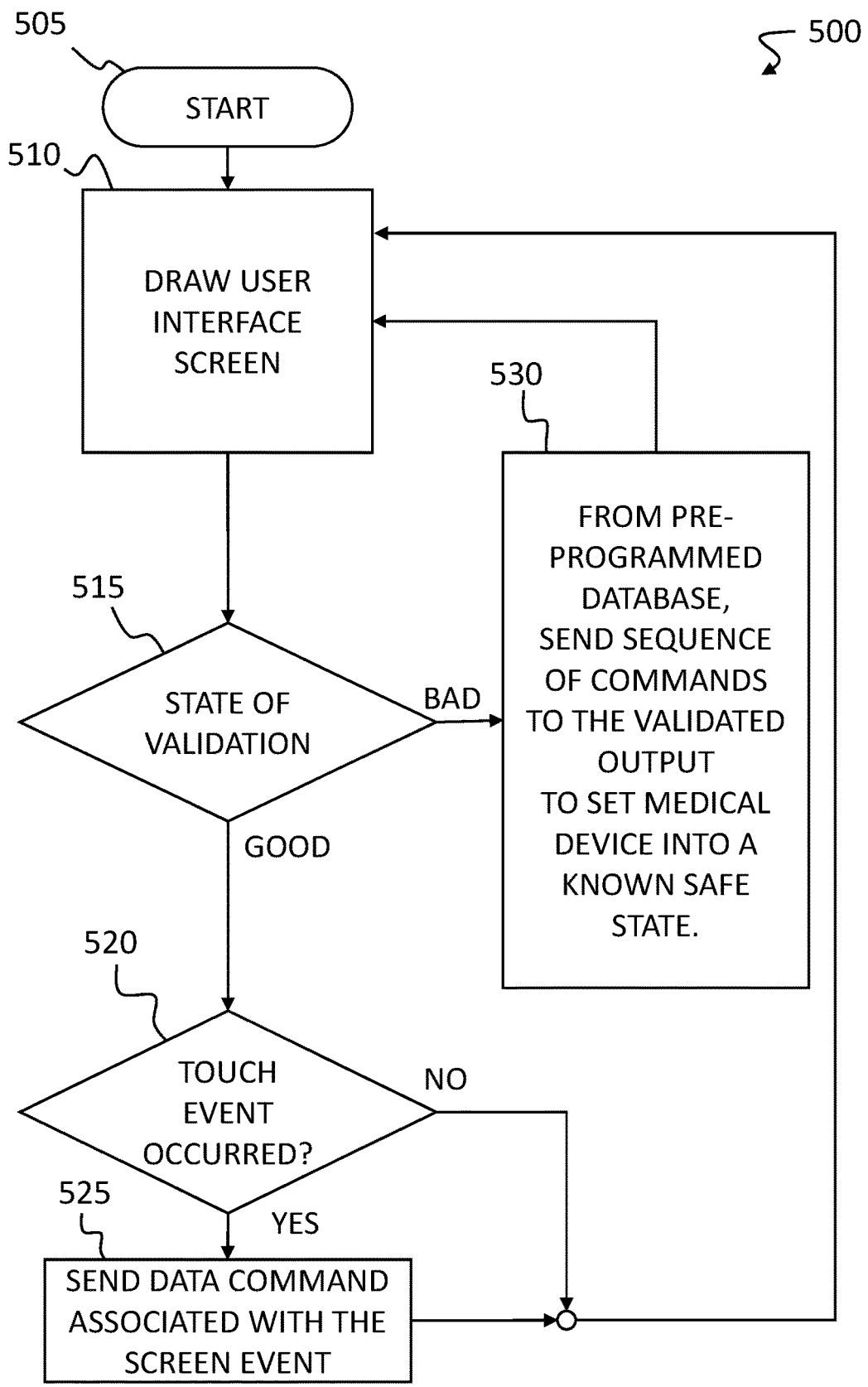
FIG. 5 depicts a flowchart of a user interface of an exemplary Self-Validating Medical Device Remote Control (SVMDRC) application.
Figure 6:
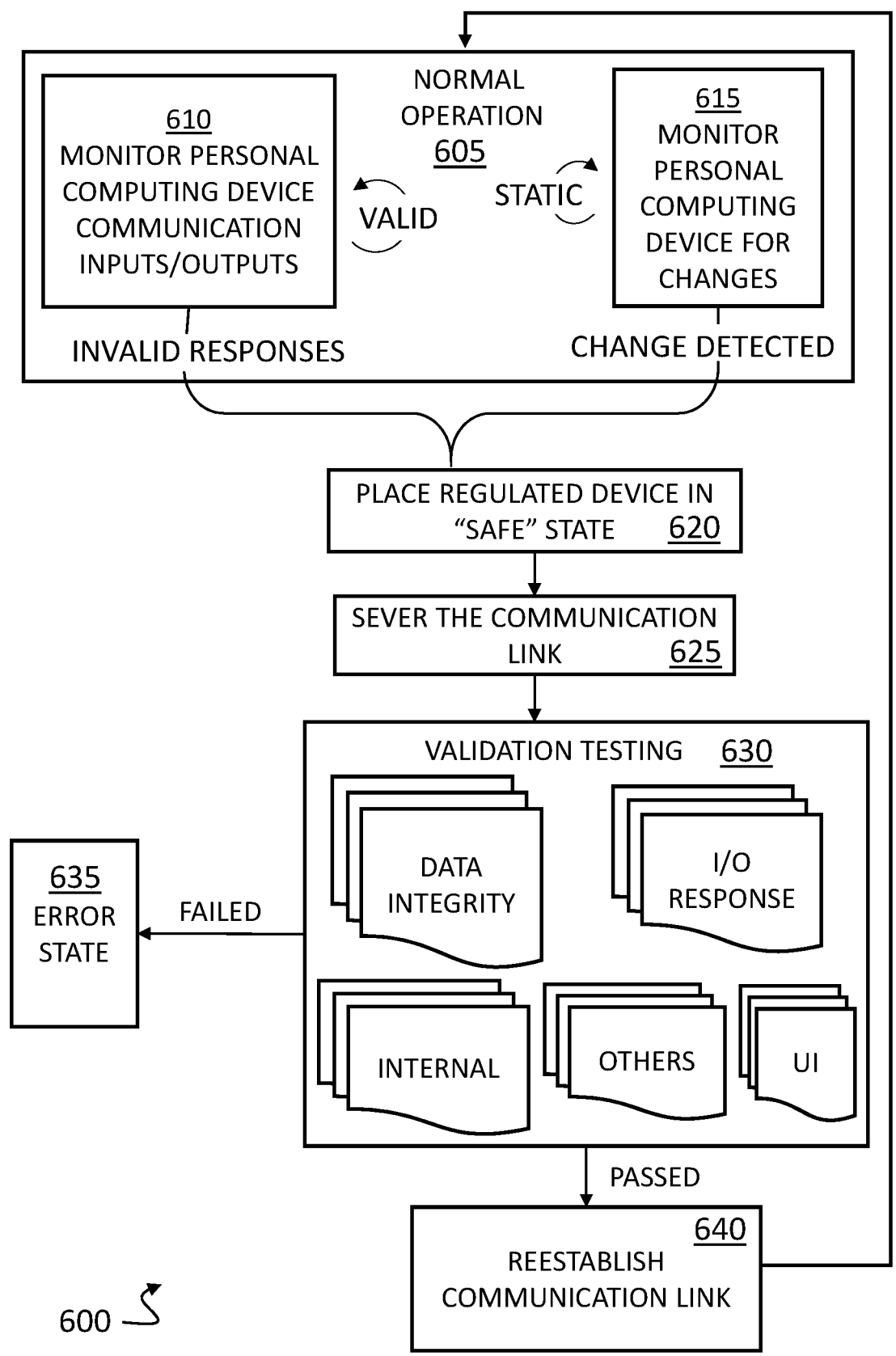
FIG. 6 depicts a flowchart of a triggered validation routine in an exemplary medical device.

FIG. 5 depicts a flowchart of a user interface of an exemplary Self-Validating Medical Device Remote Control (SVMDRC) application. An SVMDRC application 500 includes a start point 505. Control is directed from the start point 505 to drawing a user interface screen 510. After drawing the interface screen the SVMDRC application checks a state of validation 515. If the state of validation 515 is bad, as indicated by a variable or variables common to a validation engine, the control is directed to a subroutine 530 which sends a sequence of commands to the validated output from a preprogrammed database, to set the medical device into a known safe state. In some examples, designers of medical equipment may request certain command sequences be programmed in to the SVMDRC application 500, to customize the remote control to send specific commands for specific validation failures.

If the state of validation 515 is good as indicated by a variable or variables common to the validation engine, control is directed to check for touch events that may have occurred 520. If no touch events have occurred, control is directed back to drawing the user interface screen 510. If a touch event has occurred, control is directed to subroutine 525 which sends a data command associated with the screen event, to the medical device. Control then is directed back to drawing the user interface screen 510. In this way, the remote control sends commands to the medical device in response to the user presses of virtual buttons drawn in a Graphic User Interface (GUI) on a remote control display.

FIG. 6 depicts a flowchart of a triggered validation routine in an exemplary medical device. A validation routine 600 includes a normal operation subroutine 605. Within the normal operation subroutine 605 is included a communication monitoring subroutine 610 and a state change monitor 615.

In operation, an electronic self-validating module (ESVM) transceiver within a medical device receives the transmissions from a personal computing device. The communication monitoring subroutine 610 monitors the outputs of the personal computing device, for example, a mobile phone. The communications are monitored to operably validate the commands coming from the personal computing device. The ESVM within the medical device compares the commands within the communication protocol from the personal computing device, and sends them off to the medical device implementation. The medical device implementation then acts upon the command. Since the command has been validated by the ESVM, the medical implementation is assured that the command is valid.

The normal operation subroutine 605 also includes the state change monitor 615. The state change monitor 615 employs a continuous monitor of the personal computing device, to check for any changes to hardware or software within the personal computing device. For example, the state change monitor 615 may continuously monitor the version of the operating system (OS). If no changes are detected, and thus the state of the personal computing device is static, then the normal operation subroutine 605 is allowed to proceed.

If invalid responses are detected from the communication monitoring subroutine 610, or if changes are detected from the state change monitor 615, the ESVM places the medical device into a safe state. This is done because either the state of the personal computing device is no longer in a known trusted state, or the commands coming from the personal computing device are no longer within the expected range. In either of these cases, the medical device operation isolates itself from the control of the personal computing device. Since the medical device has lost its controlling system component, it places itself into a safe state 620 to protect the patient from harm. In some examples, protecting the patient may mean disconnection from power. In some examples, protecting the patient may mean continuing to provide a safe level of therapy. The specific functionality of what is a safe state may be product specific.

Once the ESVM has detected invalid responses or a change in personal computing device state, and the ESVM has placed the medical device into the safe state 620, the communication link between the medical device and the personal computing device is severed in sub-block 625. The link is severed because the communications can no longer be trusted until validation testing is successfully executed.

After the personal computing device link has been severed in sub-block 625 a validation testing subroutine 630 is executed. The validation testing subroutine 630, as depicted, includes data integrity checks, I/O response checks, internal hardware checks, and user interface checks. These checks are exemplary only. Various types of validation tests may be possible.

If the validation testing subroutine 630 results in a failed validation, the ESVM is placed into an error state 635. In some embodiments, the error state 635 may direct the state of an error pin on the ESVM to an error state. In such embodiments, medical device designers may employ the error pin on the ESVM to place the medical device in a safe state. In some embodiments, the error state 635 may direct the personal computing device to display a warning message and/or to sound an alarm. In some implementations, for example, with in a personal computing device, an error message may be sent to the ESVM, allowing the medical device to put itself into a safe state. If the validation testing subroutine 630 passes, the communication link with the personal computing device is reestablished in a sub-block 640. Once the communication link is reestablished in the sub-block 640, control is directed back to the normal operation subroutine 605. The process then repeats all over again.

In some examples, the flowchart of FIG. 6 may be implemented on the personal computing device. In such examples, the communication monitoring subroutine 610 may monitor a communication handshake from the ESVM, and may direct operation to the "invalid responses" path upon an invalid handshake response, thereby triggering a set of validation testing within the validation testing subroutine 630. Also, the state change monitor 615 may monitor changes of the app or the OS, among other changes it may be monitoring. If the user uploads a new app, operation may be directed to the "change detected" path, thereby triggering a set of validation testing within the validation testing subroutine 630. In such examples, placing the regulated device into the safe state 620 may involve the remote device sending a series of commands to the medical device to put it into a safe state.

Figure 7:
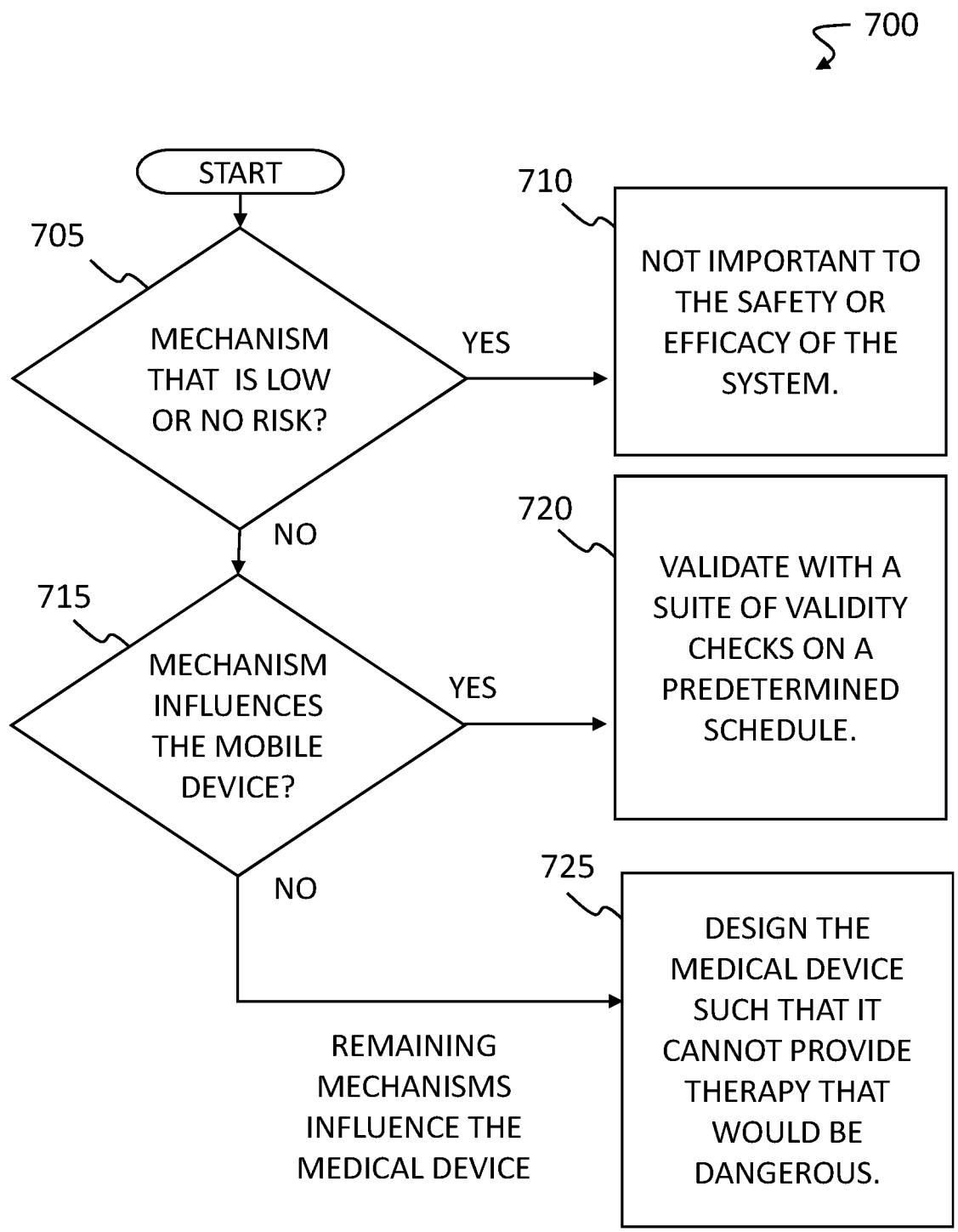
FIG. 7 depicts a risk mechanism triage of an exemplary SVS.

FIG. 7 depicts a risk mechanism triage of an exemplary SVS. Designers of medical equipment may analyze various failure mechanisms, to determine their effect on the overall safety and efficacy of the medical device. The severity level of patient harm may be scored high, medium, or low to help designers understand risk mitigation within the design. The safety and efficacy risks may be placed into three groups as depicted in FIG. 7.

A risk-mitigation triage chart 700 includes a first group of "no risk or low risk" 705, which may indicate that safety mitigations are not necessary 710. In this group, the SVS may not be required to validate the failure mechanisms.

In a second group, are "mobile device influenced" failure mechanisms 715. These failure mechanisms may cause errant functionality within the medical device. For example, if the display on the mobile device has a mirror image of the intended display, the user may press what would be considered a down button but be interpreted by the software as an up button. In such an example, the patient may get excessive therapy. Because of this risk to the patient, the mobile device may include a suite of validity checks on a predetermined schedule 720.

In a third group, where in this example, the remaining risk items will fall, are "medical device influenced" failure mechanisms. In such instances, the medical device should be designed such that it cannot provide therapy that would be dangerous 725 under any valid hardware and/or software. In this group, the SVS may not be required to validate the failure mechanisms.

In some embodiments, failure mechanisms within the third group may be validated, but only if they are within the ESVM. For example, in FIG. 2 the integrity check database 250 may contain a list of validation checks that the ESVM may provide. In some examples, the ESVM may provide various inputs from the medical device as validation inputs. In such examples, medical device designers may advantageously provide critical to function signals, for example, to the ESVM. The ESVM may be provided with functionality that may include these validation inputs within the suite of integrity checks, and may handle them the same way as the internal integrity checks.

Figure 8:
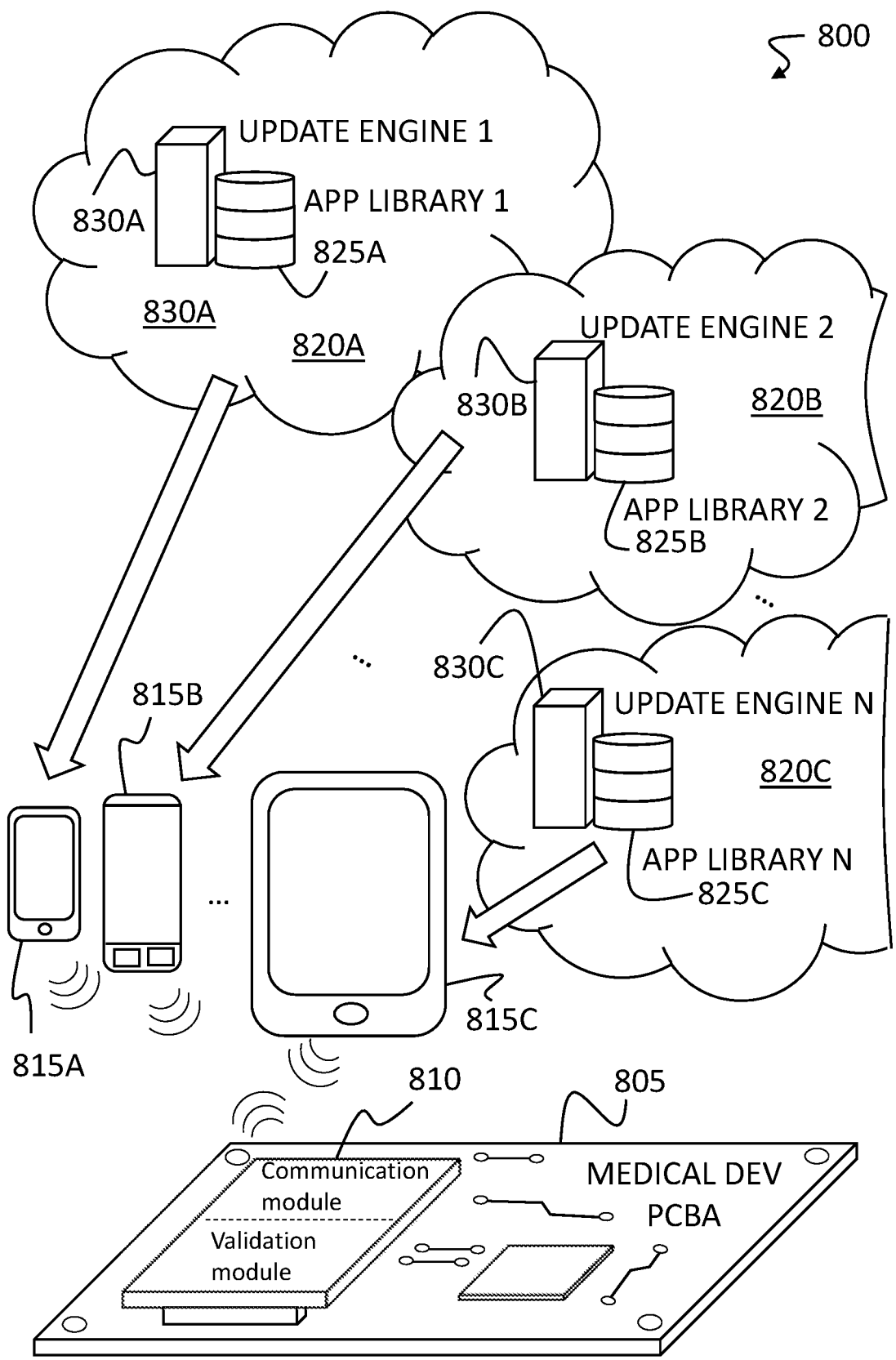
FIG. 8 depicts a cloud computing model of an exemplary SVS.

FIG. 8 depicts a cloud computing model of an exemplary SVS. A cloud computing model 800 includes a printed circuit board assembly (PCBA) 805 from a medical device. The medical device PCBA 805 includes an ESVM 810. The ESVM 810 communicates to a variety of mobile devices 815A, 815B, 815C. In some embodiments, the ESVM 810 may communicate with more than three mobile devices. The mobile devices 815A-815C receive a "mobile device, self-validating, remote medical device control" app from a cloud server network 820A, 820B and 820C. Each cloud server network 820A, 820B and 820C includes an app library 825A, 825B, and 825C. The app libraries 825A, 825B, and 825C provide an original app and updates via an update engine 830A, 830B, and 830C. In some examples, more than three mobile devices may link to more than three cloud server networks.

Although various embodiments have been described with reference to the figures, other embodiments are possible. For example, in some implementations the self-validation functionality may reside completely within a mobile device. In such implementations, the hardware and software within a medical device may remain unchanged after design validation and production validation. Thus, the medical device may remain validated as long as the device is not upgrade with new software or with new hardware. This implementation may still contain an ESVM which may contain a set number of inputs and outputs controllable by a mobile device running a custom application for the specific medical device. Further, the remote device running the custom app may display indicators and/or charts in response to the inputs on the ESVM within the medical device. Further still, the remote device may display virtual buttons that, when pressed, change the state of the outputs on the ESVM in response to presses from the user. In these implementations, the mobile device applications may employ the self-validation techniques described above. Medical device designers may advantageously employ the ESVM as a gateway to remote control using a mobile device. Medical device designers may also provide mobile apps to end customers, and may advantageously avoid revalidation each time the mobile device changes, for example, when the application versions or OS versions change.

In various examples, the SVS may provide end users convenient remote access to their medical device via a personal mobile device, for example an electronic tablet. In operation, users may gain access to heartrate data provided by a medical device transmitting the data from an ESVM within the medical device to the personal mobile device. The mobile device may display the heartrate data in various forms by employment of a mobile device application. The mobile device application may allow the user to adjust setting on the medical device by employment of button presses on the mobile device's graphic user interface (GUI).

In some examples, designers of medical devices may find advantages in employment of the ESVM within the medical device, as the remote-control device in communication with the ESVM may execute regular self-validation checks, and may keep the SVS (ESVM with remote-control device) in compliance with regulatory agencies, despite the software and/or hardware updates to the remote-control device.

In various embodiments, the remote-control device may communicate to the ESVM via a wired connection. In such implementations, the transceivers may be replaced by or supplemented by corded interfaces. In some examples, the RF transmissions between the remote-control devices and the medical devices may employ and IR communication link.

In some examples, manufacturers may provide a custom remote control device within the SVS. In such examples, the term "personal," as in "personal mobile device," may be removed and the descriptions in this document may remain applicable. Further, it will be understood that the remote control and mobile devices described need not be personal.

In various implementations of the SVMDRC, validation of the screen functionality (display and touch functions) within a mobile device, may include instructions to the user to enter their passcode, when at the same time the SVMDRC may be validating the screen functionality. In such examples, the SVMDRC may be providing validation of the mobile device, while the user may be unaware while providing tactile input to the screen.

In one exemplary aspect, an interface module is operable to interrupt unsafe commands that originate from a remote command device from being passed to a patient-applied apparatus. The interface module includes a circuit support base configured to operably couple to a medical device, and a communication module mechanically supported by the circuit support base. The communication module includes a first wireless interface adapted for communicating with a mobile communication device (MCD) over a wireless communication link. The communication module is configured to generate a command signal in response to predetermined wireless signals received from the MCD. The interface module further includes a validation module mechanically supported by the circuit support base and in operable communication with the communication module. The validation module is operable to determine whether to deliver the generated command signal to the medical device for execution by the medical device. The validation module includes a module output interface operable to communicate commands from the validation module to the medical device for execution by the medical device. The validation module further includes a validation controller operably coupled to receive the generated command signal from the communication module. The validation controller is further configured to communicate with the MCD to execute, on the MCD, a first predetermined set of validation protocols according to a first predetermined validation schedule. The validation controller is also configured to determine whether the MCD responds to the first set of validation protocol according to a first set of predetermined performance criteria. In response to determining that the MCD response does not meet the first set of predetermined performance criteria, the validation controller is configured not to transmit the generated command signal via the module output interface to the medical device for execution by the medical device.

In various embodiments, in response to determining that the MCD response meets the first set of predetermined performance criteria, the validation controller may be configured to transmit the generated command signal via the module output interface to the medical device for execution by the medical device. The validation controller may be further configured to communicate with the MCD to execute, on the MCD, a second predetermined set of validation protocols according to a second predetermined validation schedule, and to determine whether the MCD responds to the second set of validation protocol according to a second set of predetermined performance criteria. In response to determining that the MCD response does not meet the second set of predetermined performance criteria, the validation controller is configured not to transmit the generated command signal via the module output interface to the medical device for execution by the medical device. In response to determining that the MCD response meets the first set of predetermined performance criteria and the second set of predetermined performance criteria, the validation controller may be configured to transmit the generated command signal via the module output interface to the medical device for execution by the medical device.

In some implementations, the wireless communication link may include either a modulated radio frequency (RF) electromagnetic signal encoded with command data information according to a predetermined communication protocol, or a modulated optical signal encoded with command data information according to a predetermined communication protocol. Some embodiments may further include a watchdog timing module operably coupled to the validation controller and configured to cause the validation controller not to transmit the generated command signal via the module output interface to the medical device for execution by the medical device unless the watchdog timing module periodically receives a predetermined electrical signal within a predetermined timing window.

In various embodiments, the validation module may further include a data store containing a program of instructions that, when executed by the validation controller, cause the validation controller to perform operations to validate the safety and efficacy of commands received from the MCD. The operations may include detecting a predetermined trigger event associated with a change in the operation of the MCD. The operations may further include, in response to the detection of the predetermined trigger event, retrieving a predetermined validation protocol associated with the predetermined trigger event from a memory location associated with the data store. The operations may further include generating a validation request message that, when executed on the MCD, causes the MCD to perform at least one operation associated with the predetermined set of one or more validation protocols.

In some embodiments, the circuit support base may be configured to releasably couple to the medical device, and the module output interface is pluggably connectable to be in operable communication with the medical device. In various implementations, the module output interface may include a multiple contact electrical connector adapted to pluggably connect to a mating connector on the medical device.

In another exemplary aspect, an interface module is operable to interrupt unsafe commands that originate from a remote command device from being passed to a patient-applied apparatus. The interface module includes a communication module coupled to a medical device and comprising a first wireless interface adapted for communicating with a mobile communication device (MCD) over a wireless communication link, wherein the communication module is configured to generate a command signal in response to predetermined wireless signals received from the MCD. The interface module further includes a validation module in operable communication with the communication module, the validation module operable to determine whether to deliver the generated command signal to the medical device for execution by the medical device. The validation module includes a module output interface operable to communicate commands from the validation module to the medical device for execution by the medical device. The validation module further includes a validation controller operably coupled to receive the generated command signal from the communication module. The validation controller is further configured to communicate with the MCD to execute, on the MCD, a first predetermined set of validation protocols according to a first predetermined validation schedule. The validation controller is further configured to determine whether the MCD responds to the first set of validation protocol according to a first set of predetermined performance criteria. In response to determining that the MCD response does not meet the first set of predetermined performance criteria, the validation controller is configured not to transmit the generated command signal via the module output interface to the medical device for execution by the medical device.

In some embodiments, in response to determining that the MCD response meets the first set of predetermined performance criteria, the validation controller may be configured to transmit the generated command signal via the module output interface to the medical device for execution by the medical device. In various implementations, the validation controller may be further configured to communicate with the MCD to execute, on the MCD, a second predetermined set of validation protocols according to a second predetermined validation schedule. The validation controller may be further configured to determine whether the MCD responds to the second set of validation protocol according to a second set of predetermined performance criteria. In response to determining that the MCD response does not meet the second set of predetermined performance criteria, the validation controller may be configured not to transmit the generated command signal via the module output interface to the medical device for execution by the medical device.

In various implementations, in response to determining that the MCD response meets the first set of predetermined performance criteria and the second set of predetermined performance criteria, the validation controller may be configured to transmit the generated command signal via the module output interface to the medical device for execution by the medical device. In some embodiments, the validation module may further include a data store containing a program of instructions that, when executed by the validation controller, cause the validation controller to perform operations to validate the safety and efficacy of commands received from the MCD. The operations may include detecting a predetermined trigger event associated with a change in the operation of the MCD. The operations may further include, in response to the detection of the predetermined trigger event, retrieving a predetermined validation protocol associated with the predetermined trigger event from a memory location associated with the data store. The operations may further include generating a validation request message that, when executed on the MCD, causes the MCD to perform at least one operation associated with the predetermined set of one or more validation protocols. In some implementations, the validation module may be configured to releasably couple to the medical device, and the module output interface may be pluggably connectable to be in operable communication with the medical device.

In another exemplary aspect, a medical system is operable to interrupt unsafe commands that originate from a remote command device from being passed to a patient-applied apparatus. The medical system includes a housing containing a medical device configured to deliver therapy to a patient when connected to the patient, and a circuit support base configured to operably couple to a medical device. The medical system further includes a communication module coupled to the circuit support base and comprising a first wireless interface adapted for communicating with a mobile communication device (MCD) over a wireless communication link, wherein the communication module is configured to generate a command signal in response to predetermined wireless signals received from the MCD. The medical system further includes a validation module coupled to the circuit support base and in operable communication with the communication module, the validation module operable to determine whether to deliver the generated command signal to the medical device for execution by the medical device. The validation module includes a module output interface operable to communicate commands from the validation module to the medical device for execution by the medical device, and a validation controller operably coupled to receive the generated command signal from the communication module. The validation controller is further configured to communicate with the MCD to execute, on the MCD, a first predetermined set of validation protocols according to a first predetermined validation schedule. The validation controller is further configured to determine whether the MCD responds to the first set of validation protocol according to a first set of predetermined performance criteria. In response to determining that the MCD response does not meet the first set of predetermined performance criteria, the validation controller is configured not to transmit the generated command signal via the module output interface to the medical device for execution by the medical device.

In some embodiments, in response to determining that the MCD response meets the first set of predetermined performance criteria, the validation controller may be configured to transmit the generated command signal via the module output interface to the medical device for execution by the medical device. In various implementations, the validation module may further include a data store containing a program of instructions that, when executed by the validation controller, cause the validation controller to perform operations to validate the safety and efficacy of commands received from the MCD. The operations may include detecting a predetermined trigger event associated with a change in the operation of the MCD. The operations may further include, in response to the detection of the predetermined trigger event, retrieving a predetermined validation protocol associated with the predetermined trigger event from a memory location associated with the data store. The operations may further include generating a validation request message that, when executed on the MCD, causes the MCD to perform at least one operation associated with the predetermined set of one or more validation protocols. In various implementations, the circuit support base may be configured to releasably couple to the medical device, and the module output interface is pluggably connectable to be in operable communication with the medical device.

Some aspects of embodiments may be implemented as a computer system. For example, various implementations may include digital and/or analog circuitry, computer hardware, firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments may be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the first receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using Omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Fire wire, ATA/IDE, RS-232, RS-422, RS-485, 802.11 a/b/g, Wi-Fi, WiFi-Direct, Li-Fi, BlueTooth, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

In various exemplary embodiments, the SVS may enable developers and manufacturers of medical devices to reduce the burden of on-going validation testing within the development facility. Previous to the inception of the SVS, when software within a validated medical system design was changed, even if the changes were upgrades and/or improvements to the medical device design, at least a subset of validation tests were required to prove the medical device was still meeting the criteria set out in the standards for safety and efficacy. In some examples, the engineering effort to re-write, re-execute and re-document the re-validation protocols may have been greater than the effort to make the change itself. Also, it is possible that a medical device may go through multiple software releases to manufacturing and to the field, multiplying the required re-validation effort.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. An interface module operable to interrupt unsafe commands that originate from a remote command device from being passed to a patient-applied apparatus, the interface module comprising:
   a circuit support base configured to operably couple to a medical device;
   a communication module mechanically supported by the circuit support base and comprising a first wireless interface adapted for communicating with a mobile communication device (MCD) over a wireless communication link, wherein the communication module is configured to generate a command signal in response to predetermined wireless signals received from the MCD; and,
   a validation module mechanically supported by the circuit support base and in operable communication with the communication module, the validation module operable to determine whether to deliver the generated command signal to the medical device for execution by the medical device, the validation module comprising:
      a module output interface operable to communicate commands from the validation module to the medical device for execution by the medical device; and,
      a validation controller operably coupled to receive the generated command signal from the communication module, wherein the validation controller is further configured:
         (i) to communicate with the MCD to execute, on the MCD, a first predetermined set of validation protocols according to a first predetermined validation schedule; and,
         (ii) to determine whether the MCD responds to the first set of validation protocol according to a first set of predetermined performance criteria,
      wherein, in response to determining that the MCD response does not meet the first set of predetermined performance criteria, the validation controller is configured not to transmit the generated command signal via the module output interface to the medical device for execution by the medical device.

2. The interface module of claim 1, wherein, in response to determining that the MCD response meets the first set of predetermined performance criteria, the validation controller is configured to transmit the generated command signal via the module output interface to the medical device for execution by the medical device.

3. The interface module of claim 2, wherein the module output interface comprises a multiple contact electrical connector adapted to pluggably connect to a mating connector on the medical device.

4. The interface module of claim 1, wherein the validation controller is further configured:
   (iii) to communicate with the MCD to execute, on the MCD, a second predetermined set of validation protocols according to a second predetermined validation schedule; and,
   (iv) to determine whether the MCD responds to the second set of validation protocol according to a second set of predetermined performance criteria,
   wherein, in response to determining that the MCD response does not meet the second set of predetermined performance criteria, the validation controller is configured not to transmit the generated command signal via the module output interface to the medical device for execution by the medical device.

5. The interface module of claim 4, wherein, in response to determining that the MCD response meets the first set of predetermined performance criteria and the second set of predetermined performance criteria, the validation controller is configured to transmit the generated command signal via the module output interface to the medical device for execution by the medical device.

6. The interface module of claim 1, wherein the wireless communication link comprises a modulated radio frequency (RF) electromagnetic signal encoded with command data information according to a predetermined communication protocol.

7. The interface module of claim 1, wherein the wireless communication link comprises a modulated optical signal encoded with command data information according to a predetermined communication protocol.

8. The interface module of claim 1, further comprising a watchdog timing module operably coupled to the validation controller and configured to cause the validation controller not to transmit the generated command signal via the module output interface to the medical device for execution by the medical device unless the watchdog timing module periodically receives a predetermined electrical signal within a predetermined timing window.

9. The interface module of claim 1, the validation module further comprising a data store containing a program of instructions that, when executed by the validation controller, cause the validation controller to perform operations to validate the safety and efficacy of commands received from the MCD, the operations comprising:
   detect a predetermined trigger event associated with a change in the operation of the MCD;
   in response to the detection of the predetermined trigger event, retrieve a predetermined validation protocol associated with the predetermined trigger event from a memory location associated with the data store; and
   generate a validation request message that, when executed on the MCD, causes the MCD to perform at least one operation associated with the predetermined set of one or more validation protocols.

10. The interface module of claim 1, wherein the circuit support base is configured to releasably couple to the medical device, and the module output interface is pluggably connectable to be in operable communication with the medical device.

11. An interface module operable to interrupt unsafe commands that originate from a remote command device from being passed to a patient-applied apparatus, the interface module comprising:

a communication module coupled to a medical device and comprising a first wireless interface adapted for communicating with a mobile communication device (MCD) over a wireless communication link, wherein the communication module is configured to generate a command signal in response to predetermined wireless signals received from the MCD; and, a validation module in operable communication with the communication module, the validation module operable to determine whether to deliver the generated command signal to the medical device for execution by the medical device, the validation module comprising:

a module output interface operable to communicate commands from the validation module to the medical device for execution by the medical device; and, a validation controller operably coupled to receive the generated command signal from the communication module, wherein the validation controller is further configured:

(i) to communicate with the MCD to execute, on the MCD, a first predetermined set of validation protocols according to a first predetermined validation schedule; and, (ii) to determine whether the MCD responds to the first set of validation protocol according to a first set of predetermined performance criteria, wherein, in response to determining that the MCD response does not meet the first set of predetermined performance criteria, the validation controller is configured not to transmit the generated command signal via the module output interface to the medical device for execution by the medical device.

12. The interface module of claim 11, wherein, in response to determining that the MCD response meets the first set of predetermined performance criteria, the validation controller is configured to transmit the generated command signal via the module output interface to the medical device for execution by the medical device.

13. The interface module of claim 11, wherein the validation controller is further configured:

(iii) to communicate with the MCD to execute, on the MCD, a second predetermined set of validation protocols according to a second predetermined validation schedule; and, (iv) to determine whether the MCD responds to the second set of validation protocol according to a second set of predetermined performance criteria, wherein, in response to determining that the MCD response does not meet the second set of predetermined performance criteria, the validation controller is configured not to transmit the generated command signal via the module output interface to the medical device for execution by the medical device.

14. The interface module of claim 13, wherein, in response to determining that the MCD response meets the first set of predetermined performance criteria and the second set of predetermined performance criteria, the validation controller is configured to transmit the generated command signal via the module output interface to the medical device for execution by the medical device.

15. The interface module of claim 11, the validation module further comprising a data store containing a program of instructions that, when executed by the validation controller, cause the validation controller to perform operations to validate the safety and efficacy of commands received from the MCD, the operations comprising:

detect a predetermined trigger event associated with a change in the operation of the MCD;

in response to the detection of the predetermined trigger event, retrieve a predetermined validation protocol associated with the predetermined trigger event from a memory location associated with the data store;

generate a validation request message that, when executed on the MCD, causes the MCD to perform at least one operation associated with the predetermined set of one or more validation protocols.

16. The interface module of claim 11, wherein the validation module is configured to releasably couple to the medical device, and the module output interface is pluggably connectable to be in operable communication with the medical device.

17. A medical system operable to interrupt unsafe commands that originate from a remote command device from being passed to a patient-applied apparatus, the medical system comprising:

a housing containing a medical device configured to deliver therapy to a patient when connected to the patient;

a circuit support base configured to operably couple to a medical device;

a communication module coupled to the circuit support base and comprising a first wireless interface adapted for communicating with a mobile communication device (MCD) over a wireless communication link, wherein the communication module is configured to generate a command signal in response to predetermined wireless signals received from the MCD; and, a validation module coupled to the circuit support base and in operable communication with the communication module, the validation module operable to determine whether to deliver the generated command signal to the medical device for execution by the medical device, the validation module comprising:

a module output interface operable to communicate commands from the validation module to the medical device for execution by the medical device; and, a validation controller operably coupled to receive the generated command signal from the communication module, wherein the validation controller is further configured:

i. to communicate with the MCD to execute, on the MCD, a first predetermined set of validation protocols according to a first predetermined validation schedule; and, ii. to determine whether the MCD responds to the first set of validation protocol according to a first set of predetermined performance criteria, wherein, in response to determining that the MCD response does not meet the first set of predetermined performance criteria, the validation controller is configured not to transmit the generated command signal via the module output interface to the medical device for execution by the medical device.

18. The medical system of claim 17, wherein, in response to determining that the MCD response meets the first set of predetermined performance criteria, the validation controller is configured to transmit the generated command signal via the module output interface to the medical device for execution by the medical device.

19. The medical system of claim 17, the validation module further comprising a data store containing a program of instructions that, when executed by the validation controller, cause the validation controller to perform operations to validate the safety and efficacy of commands received from the MCD, the operations comprising:

detect a predetermined trigger event associated with a change in the operation of the MCD;

in response to the detection of the predetermined trigger event, retrieve a predetermined validation protocol associated with the predetermined trigger event from a memory location associated with the data store;

generate a validation request message that, when executed on the MCD, causes the MCD to perform at least one operation associated with the predetermined set of one or more validation protocols.

20. The medical system of claim 17, wherein the circuit support base is configured to releasably couple to the medical device, and the module output interface is pluggably connectable to be in operable communication with the medical device.

\* \* \* \* \*